United States Patent
Kadir (10) Patent No.: US 9,844,349 B2
(45) Date of Patent: Dec. 19, 2017

(54) METHOD FOR ESTIMATING RADIATION EXPOSURE OF A PATIENT AND RADIATION EXPOSURE MONITORING SYSTEM THEREOF

(75) Inventor: Timor Kadir, Oxford (GB)

(73) Assignee: Mirada Medical Ltd., Oxford (GB)

( * ) Notice: Subject to any disclaimer, the term of this patent is extended or adjusted under 35 U.S.C. 154(b) by 282 days.

(21) Appl. No.: 13/640,817

(22) PCT Filed: Apr. 13, 2011

(86) PCT No.: PCT/EP2011/055757
§ 371 (c)(1),
(2), (4) Date: Apr. 4, 2013

(87) PCT Pub. No.: WO2011/128350
PCT Pub. Date: Oct. 20, 2011

(65) Prior Publication Data
US 2013/0190590 A1    Jul. 25, 2013

(30) Foreign Application Priority Data

Apr. 13, 2010 (GB) .................................. 1006095.2

(51) Int. Cl.
*A61B 5/05* (2006.01)
*A61B 6/00* (2006.01)
*A61N 5/10* (2006.01)

(52) U.S. Cl.
CPC ................ *A61B 6/00* (2013.01); *A61B 6/542* (2013.01); *A61N 5/1071* (2013.01)

(58) Field of Classification Search
None
See application file for complete search history.

(56) References Cited

U.S. PATENT DOCUMENTS 3,679,902 A * 7/1972 Hurst et al. ..................... 378/97
6,650,930 B2 * 11/2003 Ding ............................. 600/436
7,519,541 B2 * 4/2009 Fackler et al. .................... 705/2
7,970,624 B2 * 6/2011 Anderson et al. ................ 705/2
(Continued)

FOREIGN PATENT DOCUMENTS

DE    19818294    11/1999
EP     1806162     7/2007
(Continued)

OTHER PUBLICATIONS

Bhatia et al., "Consistent Groupwise Non-Rigid Registration for Atlas Construction." IEEE 2004, pp. 908-911.*
(Continued)

*Primary Examiner* — James Kish
(74) *Attorney, Agent, or Firm* — Optimus Patents US, LLC (57) ABSTRACT

A method for estimating radiation exposure of a patient arising from at least one medical image study of that patient is described. The method comprises obtaining radiation exposure information relating to a plurality of procedures for which there exists a potential exposure of the patient to radiation, performing anatomical alignment of the obtained radiation exposure information to at least one reference image, estimating a radiation dose per procedure, and calculating an aggregated radiation dose based at least partly on the estimated radiation doses.

15 Claims, 5 Drawing Sheets

(56) References Cited

U.S. PATENT DOCUMENTS

| | | | |
|---|---|---|---|
| 8,238,636 B2* | 8/2012 | Roell | 382/131 |
| 2005/0041772 A1 | 2/2005 | Nishide | |
| 2006/0085223 A1* | 4/2006 | Anderson et al. | 705/2 |
| 2006/0241977 A1* | 10/2006 | Fitzgerald et al. | 705/3 |
| 2007/0263769 A1* | 11/2007 | Roell | 378/65 |
| 2008/0046286 A1* | 2/2008 | Halsted | G06F 19/322 |
| | | | 705/2 |
| 2009/0103834 A1 | 4/2009 | Jeffrey | |
| 2012/0065994 A1* | 3/2012 | Carter et al. | 705/3 |
| 2012/0148131 A1* | 6/2012 | Couch et al. | 382/131 |

FOREIGN PATENT DOCUMENTS

| | | |
|---|---|---|
| EP | 1970097 | 9/2008 |
| JP | 2010079212 | 4/2010 |

OTHER PUBLICATIONS

Huang et al., "Hybrid Image Registration based on Configural Matching of Scale-Invariant Salient Region Features." IEEE, Date of Conference: Jun. 27-Jul. 2, 2004; Date Added to IEEE Xplore: Jan. 24, 2005; Published in: Computer Vision and Pattern Recognition Workshop, 2004. CVPRW '04. pp. 1-10.*

Notification of Office Action from Intellectual Property Office in Copending British Patent Application No. GB1006095.2 dated Aug. 21, 2014, (5 pages).

* cited by examiner

METHOD FOR ESTIMATING RADIATION EXPOSURE OF A PATIENT AND RADIATION EXPOSURE MONITORING SYSTEM THEREOF

FIELD OF THE INVENTION

The field of this invention relates to a method for estimating radiation exposure. The invention is applicable to, but not limited to, a method for estimating radiation exposure of a patient and a radiation exposure monitoring system therefor.

BACKGROUND OF THE INVENTION

In the field of medical treatment, and in particular the field of radiology, there are many scanning technologies that can be used to investigate biological processes and anatomy. Such scanning technologies are typically referred to as imaging modalities and include, by way of example, X-Ray radiography, Computed Tomography (CT), Ultrasound (US), Magnetic Resonance Imaging (MRI), Single Photon Emission Computed Tomography (SPECT), Positron Emission Tomography (PET), etc. Several of these commonly used imaging modalities use ionising radiation, and as such involve exposing the patient to some level of radiation. Patients may also be exposed to radiation through other forms of medical treatment, or intervention. For example, Radiation Therapy (RT or RX), also known as Radiotherapy, is a form of intervention that may be used to treat cancers, and which involves exposing parts of a patient's body to high levels of ionising radiation.

The use of such imaging modalities and treatments/interventions that involve exposing a patient to radiation has obvious risks associated with it, including short term risks such as radiotoxicity as well as long term effects such as an increased risk of cancer. Over the past two decades there has been a rapid increase in the use of imaging in medical practice, including the use of imaging modalities that use ionising radiation, such as X-Ray radiography, Computed Tomography (CT), Single Photon Emission Computed Tomography (SPECT), Positron Emission Tomography (PET), etc. The increased use of such imaging modalities has a direct effect on the amount of radiation a patient may be exposed to, both over a short period of time as well as over the lifetime of that patient, and thereby on the associated risks to the patient.

Thus, a need exists for an improved radiation exposure monitoring system and method of operation therefor.

SUMMARY OF THE INVENTION

Accordingly, the invention seeks to mitigate, alleviate or eliminate one or more of the above mentioned disadvantages singly or in any combination. Aspects of the invention provide a method for estimating radiation exposure of a patient and a radiation exposure monitoring system as described in the appended claims.

According to a first aspect of the invention, there is provided a method for estimating radiation exposure of a patient. The method comprises obtaining radiation exposure information comprising at least one medical image relating to at least one procedure for which there exists a potential exposure of the patient to radiation, performing anatomical alignment of the obtained radiation exposure information, estimating a radiation dose per procedure based on the at least one medical image, and calculating an aggregated radiation dose based at least partly on the estimated radiation doses.

In one example embodiment of the invention, an aggregated estimate of radiation exposure resulting from a plurality of procedures, and a plurality of types of procedure, for which information is obtained, may be calculated. Furthermore, by anatomically aligning obtained information, an anatomical association may be achieved between the different procedures for which information has been obtained, thereby enabling an aggregated estimate of radiation exposure to be localised with respect to specific body parts of the patient According to an optional feature of the invention, the method may comprise obtaining information relating to at least one from a group consisting of: at least one procedure previously performed on the patient for which there exists a potential for the patient to have been exposed to radiation; and at least one prospective procedure yet to be performed on the patient for which there exists a potential for exposure of the patient to radiation. In this manner, an aggregated estimate of radiation exposure may be calculated for previously performed procedures for a patient, and for prospective procedures yet to be performed on a patient, either independently or in combination with procedures already performed on the patient, for which there exists a potential for exposure of the patient to radiation.

According to an optional feature of the invention, the method may comprise obtaining information relating to procedures comprising at least one from a group consisting of:
  at least one X-Ray radiography scan;
  at least one Computed Tomography (CT) scan;
  at least one Single Photon Emission Computed Tomography (SPECT) scan;
  at least one Positron Emission Tomography (PET) scan;
  at least one nuclear medicine scan;
  at least one planar bone scan;
  at least one barium enema scan; and
  at least one radiation therapy procedure.

According to an optional feature of the invention, obtaining information relating to the at least one procedure for which there exists a potential exposure of the patient to radiation may comprise retrieving such information from at least one from a group consisting of: at least one remote data source, at least one local data source.

According to an optional feature of the invention, obtaining radiation exposure information for the at least one procedure may comprise obtaining at least one anatomical image associated therewith.

According to an optional feature of the invention, performing anatomical alignment of the obtained radiation exposure information may comprise aligning the at least one anatomical image associated with each procedure to at least one reference image. The at least one reference image may comprise at least one anatomical image associated with the at least one procedure to which obtained radiation exposure information relates. The at least one anatomical image associated with the at least one procedure to which obtained radiation exposure information relates may be selected to provide the at least one reference image, based at least partly on at least one from a group consisting of:
  a type of procedure with which the at least one anatomical image is associated;
  a comprehensiveness of anatomical coverage of the at least one anatomical image;
  a resolution of the at least one anatomical image;

information density of at least one anatomical image; and information content of at least one anatomical image.

According to an optional feature of the invention, the at least one reference image may comprise at least one generic anatomical image. The at least one generic anatomical image may be selected to provide the at least one reference image from a plurality of generic anatomical images, based at least partly on at least one from a group consisting of:
- patient gender;
- patient height;
- patient weight; and
- patient lean body mass.

According to an optional feature of the invention, performing anatomical alignment of the obtained radiation exposure information may comprise performing group-wise alignment of the at least one anatomical image associated with obtained radiation exposure information sequentially to one another.

According to an optional feature of the invention, performing anatomical alignment of the obtained radiation exposure information may comprise aligning the radiation exposure information to anatomical regions within a predefined set of anatomical regions.

According to an optional feature of the invention, estimating a radiation dose per procedure may be based at least partly on at least one from a group consisting of:
- a type of procedure for which a radiation dose is being estimated;
- at least one procedural specific attribute;
- at least one body part specific attribute;
- a volume of tissue exposed to radiation;
- at least one patient specific attribute.

According to an optional feature of the invention, the method may further comprise calculating anatomically localised aggregated radiation doses based at least partly on at least one estimated radiation dose. The method may comprise calculating anatomically localised aggregated radiation doses categorised into types of radiation. The method may further comprise comparing at least one calculated aggregated radiation dose to at least one threshold value, and if the at least one calculated aggregated radiation dose exceeds the at least one threshold value, generating a warning message.

According to a second aspect of the invention, there is provided a radiation exposure monitoring system comprising signal processing logic. The signal processing logic is arranged to obtain radiation exposure information comprising at least one medical image relating to procedures for which there exists a potential exposure of the patient to radiation, perform anatomical alignment of the obtained radiation exposure information, estimate a radiation dose per procedure based on the at least one medical' image, and calculate an aggregated radiation dose based at least partly on the estimated radiation doses.

According to a third aspect of the invention, there is provided an integrated circuit for monitoring radiation exposure. The integrated circuit comprises signal processing logic arranged to obtain radiation exposure information comprising at least one medical image relating to procedures for which there exists a potential exposure of the patient to radiation, perform anatomical alignment of the obtained radiation exposure information, estimate a radiation dose per procedure based on the at least one medical image, and calculate an aggregated radiation dose based at least partly on the estimated radiation doses.

According to a fourth aspect of the invention, there is provided a tangible computer program product having executable program code stored therein for programming signal processing logic to perform a method for estimating radiation exposure of a patient. The program code is operable for, when executed at a computer system, obtaining radiation exposure information comprising at least one medical image relating to procedures for which there exists a potential exposure of the patient to radiation, performing anatomical alignment of the obtained radiation exposure information, estimating a radiation dose per procedure based on the at least one medical image, and calculating an aggregated radiation dose based at least partly on the estimated radiation doses.

These and other aspects of the invention will be apparent from, and elucidated with reference to, the embodiments described hereinafter.

BRIEF DESCRIPTION OF THE DRAWINGS

Further details, aspects and embodiments of the invention will be described, by way of example only, with reference to the drawings. Elements in the figures are illustrated for simplicity and clarity and have not necessarily been drawn to scale. Like reference numerals have been included in the respective drawings to ease understanding.

FIG's 2 and 3 illustrate examples of anatomical images.

DETAILED DESCRIPTION

Examples of the invention will be described in terms of a server side radiation exposure monitoring system arranged to implement a method for estimating radiation exposure of a patient according to some example embodiments of the present invention, and to make available calculated radiation doses to client side user interface applications. However, it will be appreciated by a skilled artisan that the inventive concept herein described may be embodied in any type of radiation exposure monitoring system.

Figure 1:
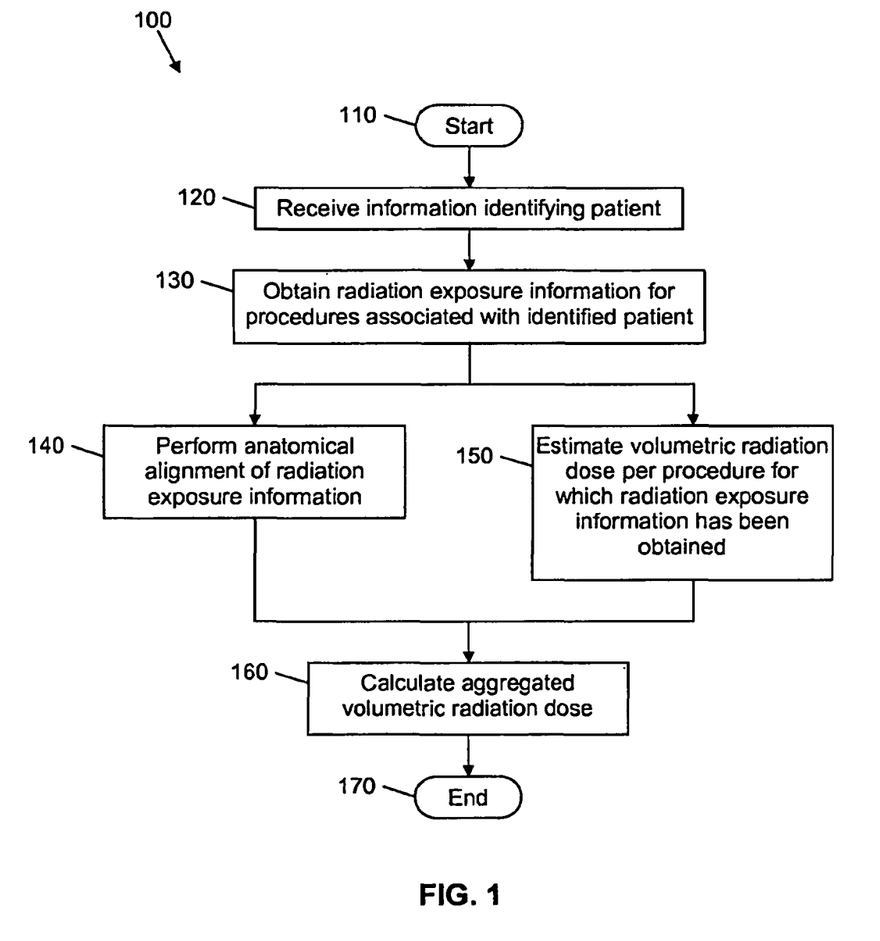
FIG. 1 illustrates a simplified flowchart of an example of a method for estimating radiation exposure of a patient.

Referring to FIG. 1, there is illustrated a simplified flowchart 100 of an example of a method for estimating radiation exposure of a patient according to some example embodiments. In summary, the method comprises obtaining radiation exposure information relating to at least one procedure for which there exists a potential exposure of the patient to radiation, performing anatomical alignment of the obtained radiation exposure information, estimating a radiation dose per procedure, and calculating an aggregated radiation dose based at least partly on the estimated radiation doses. In this manner, an aggregated estimate of radiation exposure resulting from one or more procedures for which information is obtained may be calculated. Furthermore, by anatomically aligning obtained information, an anatomical association may be achieved between the different procedures for which information has been obtained, thereby enabling an aggregated estimate of radiation exposure to be localised with respect to specific body parts of the patient.

More specifically for the example illustrated in FIG. 1, the method starts at step 110, and moves on to step 120 where information identifying a patient, for which radiation exposure is to be estimated, is received. For example, information identifying the patient may be provided by a user. Such information may comprise, by way of example only, patient name, demographic details, address, a patient identification number, etc.

Next, information relating to procedures for which there exists a potential exposure of the patient to radiation is obtained at step 130. For example, such radiation exposure information may comprise information relating to one or more procedures previously performed on the patient for which there exists a potential for the patient to have been exposed to radiation. In this manner, an aggregated estimate of radiation exposure may be calculated for procedures already performed on a patient. It is contemplated that such radiation exposure information may additionally (or alternatively) comprise information relating to one or more prospective procedures yet to be performed on the patient, for which there exists a potential for exposure of the patient to radiation. In this manner, an aggregated estimate of radiation exposure may be calculated for prospective procedures yet to be performed on a patient, either independently or in combination with procedures already performed on the patient, for which there exists a potential for exposure of the patient to radiation.

Such information obtained may relate to any type of procedure for which there exists a potential exposure of the patient to radiation, such as any type of procedure involving ionising radiation. For example, information may be obtained relating to one or more of:
  one or more X-Ray radiography scans;
  one or more Computed Tomography (CT) scans;
  one or more Single Photon Emission Computed Tomography (SPECT) scans;
  one or more Positron Emission Tomography (PET) scans;
  one or more nuclear medicine scans;
  one or more planar bone scans;
  one or more barium enema scans;
  one or more radiation therapy procedures;
  etc.

The information relating to procedures for which there exists a potential exposure of the patient to radiation may be stored within one or more local data sources and/or one or more remote data sources. Accordingly, it is contemplated that obtaining information relating to procedures for which there exists a potential exposure of the patient to radiation may comprise retrieving such information from one or more remote data sources and/or one or more local data sources, as described in greater detail below with reference to FIG. 4.

Having obtained information relating to procedures for which there exists a potential exposure of the patient to radiation, the method moves on to steps 140 and 150. At step 140, anatomical alignment of the obtained radiation exposure information is performed. For example, obtaining radiation exposure information for a procedure may comprise obtaining one or more anatomical images associated therewith. Accordingly, performing anatomical alignment of the obtained radiation exposure information may comprise aligning the one or more anatomical images associated with each procedure to one or more reference images. It will be appreciated that for procedures involving imaging modalities, such procedures inherently produce anatomical images for relevant parts of the patient's body. Accordingly, such images may be used for this purpose, and aligned to one or more reference images. For procedures that do not directly involve imaging modalities, for example procedures involving therapeutic radiation exposure such as radiation therapy, typically such procedures will involve delivering doses of radiation to the patient in accordance with radiation dose plans, such radiation dose plans typically comprising volumetric datasets of doses which correspond to a previously produced scan of the patient. Accordingly, it is contemplated that such a scan to which radiation dose plans of a non-imaging modality procedure correspond may be used to provide an anatomical image for that procedure to be aligned to one or more reference images. Conversely, where such a non-imaging modality procedure involves non-volumetric doses of radiation, such as whole body part irradiation, that procedure may be simply 'aligned' to the entire body of the patient. In accordance with some example embodiments, for procedures that do not involve imaging modalities, one or more conceptual illustrations of at least a part of the human anatomy (as opposed to, say, a scan of a part of an actual human body) may be used to provide anatomical images.

In accordance with some example embodiments, the one or more reference images may comprise one or more of the anatomical images associated with the procedures to which obtained radiation exposure information relate. For example, a procedure-related anatomical image comprising a largest field of view of the patient may be selected to provide a reference image, thereby providing a most comprehensive anatomical coverage of the patient within a single reference image. Alternatively and/or additionally, the quality and/or resolution of an image may be a determining factor as to whether or not a procedure-related anatomical image is selected to provide a reference image. For example, a quality and/or resolution of such an image may typically be dependent upon the imaging modality used to produce the image. Accordingly, the selection of one or more anatomical images associated with the procedures to which obtained radiation exposure information relates may be based on a hierarchy of procedure type. An example of such a procedure type hierarchy may comprise the following or at least something similar to:

CT>MR>PET>SPECT>X-Ray

Where: CT=Computed Tomography, MR=magnetic resonance, PET=Positron Emission Tomography, SPECT=Single Positron Emission Computed Tomography.

As will be appreciated, magnetic resonance imaging uses an electromagnetic field to produce an image, as opposed to ionised radiation. Accordingly, a patient will generally not be exposed to radiation during such a procedure. However, because such an imaging modality produces high resolution images, it is contemplated that information relating to such a non-radiation procedure may be obtained along with information relating to procedures that use ionised radiation, and such non-radiation information used to provide (or at least considered as possible being used to provide) a reference image. Thus, information from imaging modalities that do not involve exposure to radiation may be used to help align the information from procedures that do involve exposure to radiation.

The use of such a procedure type hierarchy to select one or more reference images may be used in combination with, say, a field of view of the images. In this manner, an image may be selected based not just on its quality/resolution, but also on, for example, its comprehensiveness of anatomical coverage, etc. Furthermore, procedure specific attributes that affect the quality and/or resolution of an image obtained via a specific type of procedure may be taken into consideration when selecting a reference image. For example, in CT scans a higher tube current generally gives rise to a greater image quality. A similar relationship operates for conventional X-ray scans. In magnetic resonance (MR) scans, the pulse sequence used for the acquisition determines the type of tissue detail visible in the scan. Certain sequences give rise to high contrast between different tissue types whereas others result in higher image frame rates and so forth. Accordingly, such procedure specific attributes that give rise to a higher tissue contrast within resulting images may also be used when selecting a reference image. Such information is typically encoded in the meta-data associated with the image data, for example in the tags/header of a Digital Imaging Communications in Medicine (DICOM) file.

Accordingly, it is contemplated that for some example embodiments, one or more of the anatomical images associated with the procedures to which obtained radiation exposure information relates may be selected to provide one or more reference images, based at least partly on, say, at least one from a group consisting of: a type of procedure with which the at least one anatomical image is associated, a comprehensiveness of anatomical coverage of the at least one anatomical image, a quality and/or resolution of the at least one anatomical image, etc.

Figure 2:
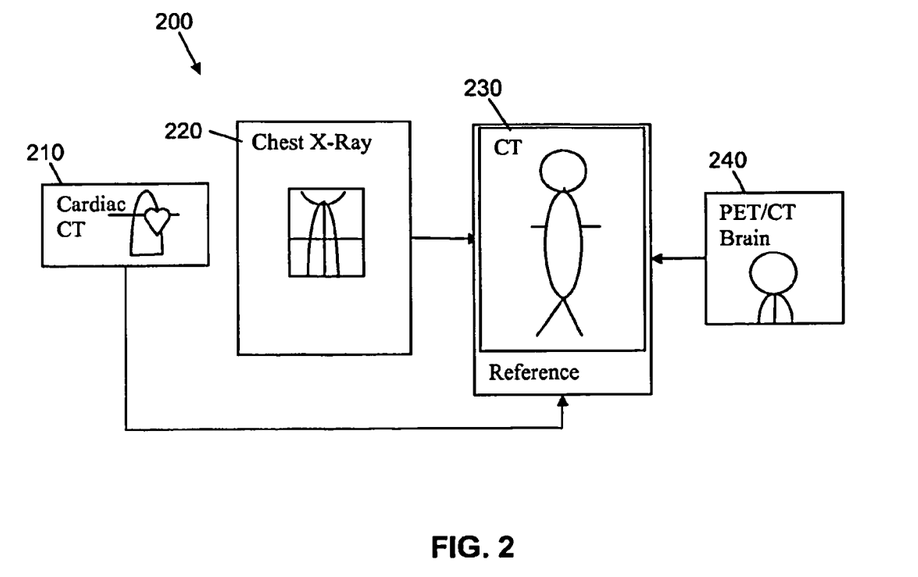
Figure 3:
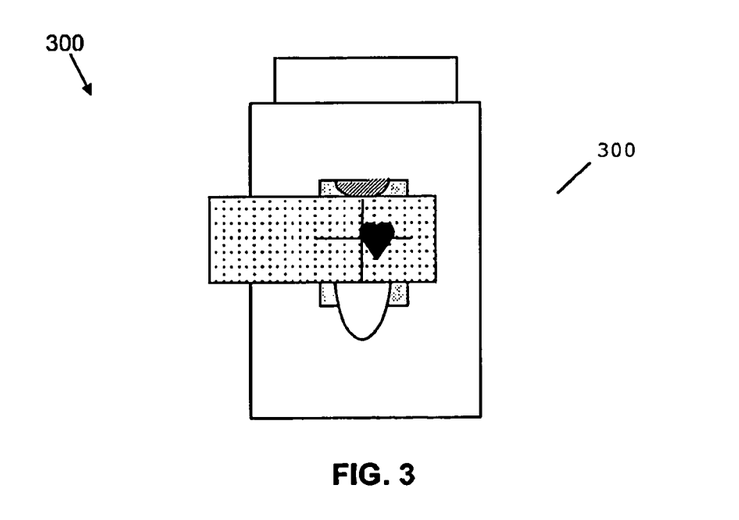

For example, referring to FIG. 2, there are illustrated examples of four anatomical images that may be associated with procedures to which obtained radiation exposure information relates. A first image 210 comprises a cardiac CT scan of the patient, and as such comprises an anatomical coverage localised to the cardiac region of the patient's body. A second image 220 comprises a chest X-Ray of the patient, and as such comprises an anatomical coverage localised to the chest region of the patient's body. A third image 230 comprises a CT scan of the patient's entire body, and as such comprises a full anatomical coverage of the patient's body. Finally, a fourth image 240 comprises a PET brain scan of the patient, and as such comprises an anatomical coverage localised to the head region of the patient's body. CT imaging modalities produce high quality/resolution images, and as such the first and third images 210, 230 may be considered as possible reference images with which to align the other images. The third image has the additional benefit of comprising a full anatomical coverage of the patient's body. Accordingly, based on the procedure with which this image is associated (i.e. a CT scan), and the comprehensiveness of the image's anatomical coverage (i.e. full body coverage), the third image 230 may be selected to provide a reference image with which to align the other images. FIG. 3 illustrates the images 210, 220, 230, 240 of FIG. 2 being aligned to the reference image, which for the illustrated example comprises image 230.

Other factors may additionally and/or alternatively be taken into consideration when determining the suitability of an image to act as a reference image. For example, the suitability of an image may be determined based on other factors, such as information density, for example based on a density of voxels per unit volume, and/or an estimate of the information content using measures such as entropy or mutual information.

According to some alternative example embodiments, it is contemplated that one or more reference images with which the obtained radiation exposure information is aligned may comprise one or more generic anatomical images. For example, such a generic anatomical image may comprise an illustration of at least a part of a human anatomy, which may be used as an anatomical model or 'atlas' to which the radiation exposure may be aligned. Alternatively, such a generic anatomical image may comprise an image of an actual human anatomy, for example of a different patient or of a test subject. By using a generic anatomical image in this manner, the need to select one or more images associated with the procedures to which obtained radiation exposure information relates as (a) reference image(s) may be avoided. It is contemplated that a plurality of generic anatomical images used to cover variations in anatomical characteristics, such as gender, height, weight/build, lean body mass, etc., may be available. In this manner, a generic anatomical image may be selected based on such characteristics in order to provide a 'best fit' anatomical reference image for the patient.

It is further contemplated that a solution of an appropriate reference image may be updated/adapted over time as new information comprising anatomical images becomes available, for example from subsequently performed procedures.

According to some further alternative example embodiments, it is contemplated that the obtained radiation exposure information may be aligned by way of group-wise alignment, whereby the anatomical images associated with the obtained radiation exposure information are sequentially aligned to one another, rather than to a reference image. An example of such a group-wise alignment technique is described in "Consistent group-wise non-rigid registration for atlas construction" [K. K. Bhatia, J. V. Hajnal], which is incorporated herein by reference. In this manner, the need to either select one or more reference images from the obtained information, or to specify/provide one or more generic reference images, may be avoided.

Alternatively, it is contemplated that the obtained radiation exposure information may be aligned by building a composite reference set, where anatomical images for the different procedures for which radiation exposure information incrementally improve the overall, composite reference as they are added to it. For example, if an initial reference dataset comprises an upper-body CT scan, and a subsequent data set comprising an MRI scan is available that images the abdomen down to the thighs, then once these two datasets have been registered within the composite reference set, they may provide a reference for the alignment of subsequent datasets, either separately or in a group-wise registration scheme.

In one example embodiment, the radiation exposure information may be aligned to the reference image(s) (or to one another in the case of group-wise alignment) in any suitable manner, such as by way of imaging registration whereby the different sets of data for the obtained radiation exposure information are transformed into a single coordinate system. For example, in the case of three dimensional (3D) data, such as produced by CT imaging, mono-modal or multi-modal registration algorithms may be used to perform an initial rigid alignment of the radiation exposure information. An example of such an algorithm is the alignment of medical images using mutual information as described in "Alignment by Maximization of Mutual Information", published in the International Journal of Computer Vision, 24(2) pg 137-154, 1997 Paul Viola and William M. Wells III. A further, deformable alignment may then be performed to compensate for non-rigid variations in the patient's image, due to, for example, positioning variations, weight loss/gain, etc. In the case of two dimensional (2D) data, such as produced by planar nuclear medicine (NM) or X-Ray imaging modalities, 2D to 3D registration may be performed on the data. Techniques for performing such 2D to 3D registration are known. One such known technique comprises projecting 3D reference data into a 2D space, and then aligning the 2D radiation exposure information with the projected 2D reference data. Such an approach is described in "A patient-to-computed-tomography image registration method based on digitally reconstructed radiographs." [L Lemieux, R Jagoe, D R Fish, N D Kitchen, DGT. Med. Phys. Volume 21, Issue 11, pp. 1749-1760 (November 1994)], which is incorporated herein by reference.

It is contemplated that, in addition to performing such image registration to align the obtained radiation exposure information, it may be necessary to perform pre-matching of the obtained information in cases where, say, the fields of view of images associated with obtained radiation exposure information being aligned are very different. For example, the alignment of a whole body scan with a scan of a cardiac left ventricle will typically comprise very different fields of view. Accordingly, a conventional image registration technique is likely to fail. Thus, performing pre-matching to initialise the alignment of, say, two images can substantially alleviate such a problem. One known approach for such pre-matching comprises detecting salient landmarks within each image (or data set) and then using a point matching algorithm to align the detected landmarks. Such an approach is described in "Hybrid Image Registration based on Configural Matching of Scale-Invariant Salient Region Features" [X. Huang, Y. Sun, D. Metaxas, F. Sauer, and C. Xu], which is incorporated by reference herein. An alternative approach is to detect known anatomical landmarks in each image (or data set) and to use these to perform an initial alignment. Such an approach is described in "Simultaneous registration and landmark detection." [S. L. Bond, J. M. Brady. Proc IEEE Eng Med Biol Soc. 2006; 1:2634-7] and which is also incorporated by reference herein.

With a single procedure for which radiation exposure information is obtained, it is contemplated that a number of images may be acquired. Typically these images would be taken whilst the patient remains in the same position within (or with respect to) the imaging machine, and the spatial relationship between such images may be encoded within the imaging file format, such as a Digital Imaging Communications in Medicine (DICOM) file format. Accordingly, such images may be considered as sharing a common frame of reference, and thus may be aligned to other radiation exposure information as a set, without the need for such related images to be aligned to one another. However, it will be appreciated that even within such a set of related images, there may be a small amount of body or organ motion between the images within a single procedure. Accordingly, it may be desirable to perform a small amount of alignment between the images in a set to compensate for such small variations.

In accordance with some alternative example embodiments, the radiation exposure information may simply be aligned to (associated with) one or more anatomical regions within a predefined set of anatomical regions, as opposed to being aligned to an image. For example, each radiation exposure information record may be associated with a list of anatomical regions. An aggregated dose may then be determined for each anatomical region separately. Although this would not provide such a high level of resolution for identifying those regions of the body that have been exposed to radiation, it would provide a simplified solution.

Referring back to FIG. 1, and specifically to step 150, the volumetric radiation dose per procedure for which radiation exposure information has been obtained is estimated. This step estimates the radiation exposure for each procedure actually performed. Radiation exposure is a function of many parameters. The most important factor is typically the type of procedure. For example a CT scan will expose only those parts of the patient's body that were imaged, whereas nuclear medicine (NM) scans, such as planar bone scanning or PET, will expose the whole body systematically, since it involves injection of a radioactive compound. In the case of the latter, the exposure per body part will also vary according to the precise nature of the tracer used and its biodistribution. Therefore, the approach to estimate radiation exposure for an individual procedure may depend upon the type of procedure and the parameters of that procedure. Furthermore, the exposure to radiation from a procedure will vary depending upon the subject, for example on attributes of the patient (e.g. height, weight, lean body mass, etc.), as well as the particular part of the body exposed to the radiation. Accordingly, it is contemplated that estimating a radiation dose per procedure may be based at least partly on one or more from a group consisting of: a type of procedure for which a radiation dose is being estimated, one or more procedural specific attributes (parameters), one or more body part specific attributes, a volume of tissue exposed to radiation, one or more patient specific attributes, etc.

Any suitable known method for estimating the radiation exposure of a procedure may be used to estimate the radiation exposure of a procedure for which radiation exposure has been obtained. Advanced dosimetric techniques have been developed to produce estimates for radiation exposure for both internal source, e.g. PET, and external source, e.g. CT, radiation. In one approach, pre-defined lookup tables may be used to produce an estimate of the radiation. The lookup tables may contain one or more entries for each type of procedure of interest and a representative estimate of the radiation dose. Each estimate may be in a form that relates to the radiation per unit volume of tissue and therefore could be used to build an overall volumetric radiation estimate. The estimates in the table may be derived for common variations of different procedures, and may be augmented by information related to hospital—specific imaging protocols. For example, it is envisaged that a medical physics department of the hospital could add entries for common imaging scans used at that site.

A more sophisticated approach may use lookup tables that are able to be modulated by the most significant scan parameters associated with radiation. For example, the lookup table may comprise estimates of radiation for different types of procedure, where these can be adjusted to account for patient specific variables, such as weight, lean body mass and so forth, and also imaging parameters such as, in the case of an X-Ray imaging procedure, X-ray tube current, voltage, scanning pitch, and so forth. Standard interpolation and extrapolation methods may be used to produce more accurate and patient specific estimates. It should be noted that medical image files typically contain a large set of parameters about the image acquisition that can be used to estimate radiation doses.

An alternative approach may comprise the use of dosimetric techniques to build an accurate and patient specific estimate of radiation exposure. There are many such techniques known that range from simple equations that require only image equipment parameters through to sophisticated techniques that take into account the anatomy of the patient and precise sources of radiation and types of radiation. Such techniques are known in the field of medical physics, and examples of which are described in "Patient Dosimetry for X-RAYS used in Medical Imaging." [Journal of the ICRU .2005; 5: iv-vi] and http://www.impactscan.org/slides/impactcourse/principles%20of%20ct%20dosimetry/index.html, which are incorporated herein by reference. Such dosimetric techniques may be used to populate the look-up tables described above.

It will be appreciated that steps 140 and 150 are not limited to being performed substantially simultaneously, such as illustrated in FIG. 1, but rather may be performed sequentially. For example, it is contemplated that step 140 may be performed prior to step 150. In this manner, the spatial correspondence of radiation exposure information for one procedure may be used to facilitate the estimation of the dose of radiation exposure for another procedure. For example, where radiation exposure has occurred to parts of a patient's body that were not imaged (e.g. for a PET scan of a patient's head only the head region may be imaged even though the exposure to radiation is substantially throughout the patient's entire body), one or more images covering the rest of the patient's body from other procedures may be used to produce a more accurate and localised radiation dose estimate.

Referring back to FIG. 1, having anatomically aligned the radiation exposure information and estimated volumetric radiation doses for the procedures for which radiation exposure information has been obtained, the method moves on to step 160, where an aggregated volumetric radiation dose is calculated. Specifically, this step may comprise combining the result of anatomically aligning the obtained radiation exposure information performed at step 140 and the result of estimating radiation doses for each procedure for which radiation exposure information has been obtained in step 150 to calculate an estimate of an aggregated radiation dose. The aggregated volumetric radiation dose may comprise a single aggregated radiation dose value that is representative of an overall exposure of the patient's body to radiation. Alternatively, it is contemplated that one or more estimates for anatomically localised aggregate radiation doses may be calculated, whereby such estimates may comprise one or more aggregated radiation dose value(s) that is/are representative of a more anatomically localised exposure to radiation for one or more parts of the patient's body. For example, one or more radiation dose estimates for individual procedures may be mapped to the reference image(s). In accordance with some example embodiments, this step may comprise calculating anatomically localised aggregated radiation doses categorised into types (class) of radiation, e.g. alpha radiation, beta, radiation, gamma radiation, etc. Furthermore, the provision of such aggregated radiation doses enables the mapping of aggregated radiation exposure, class of radiation exposure, time and duration of radiation exposure, etc. in order to enable the assessment of both short term and long term risks.

Thus, in this manner, one or more aggregated radiation doses may result from a range of different types of procedures, and in particular from a combination of procedures comprising external radiation sources, such as X-ray scans, and procedures comprising internal radiation sources, such as PET scans.

For the illustrated example, the method then ends at 170.

Figure 4:
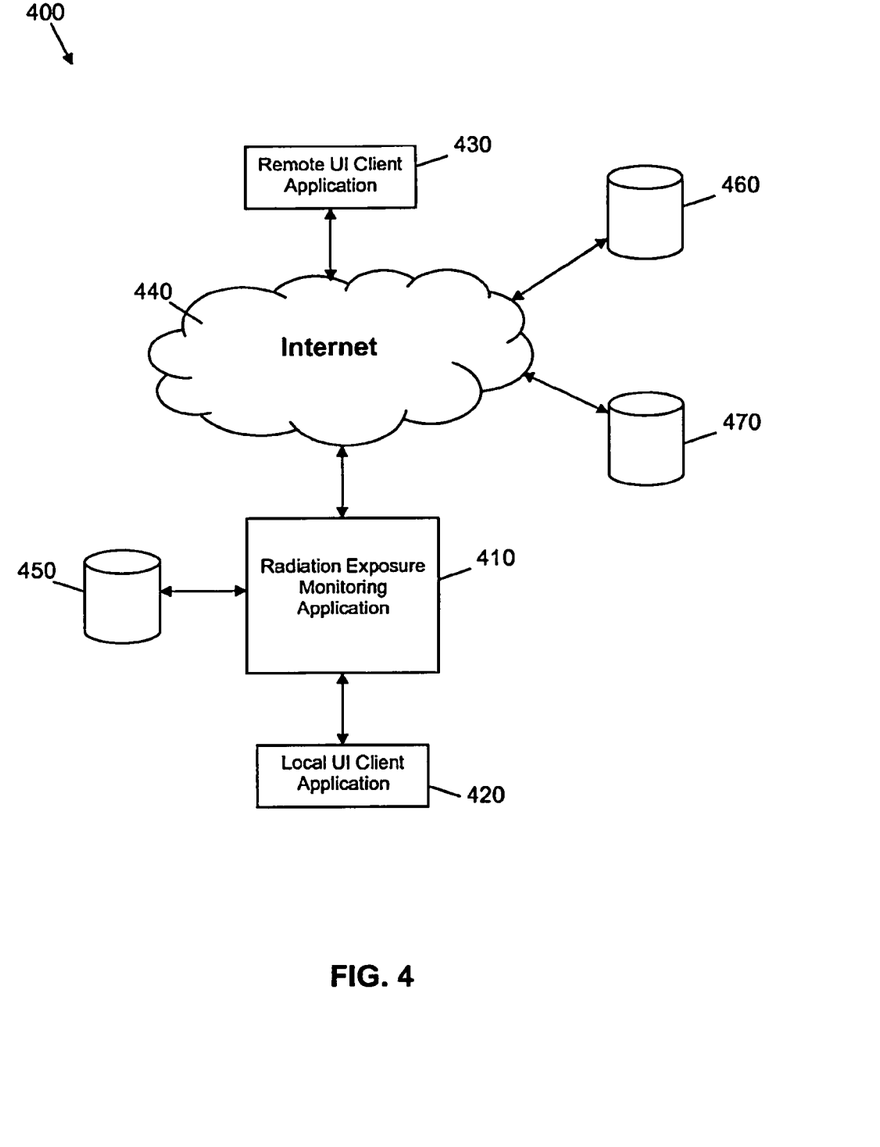
FIG. 4 illustrates a block diagram of an example of a radiation exposure monitoring system.

Referring now to FIG. 4, there is illustrated a block diagram of an example of a radiation exposure monitoring system 400 adapted in accordance with some example embodiments of the present invention. Such a system may comprise, or form a part of, a picture archiving and communication system (PACS), radiological information system (RIS), hospital information system (HIS), advanced visualisation workstations, imaging acquisition workstations, web-based or cloud-based medical information and image systems, etc. For the illustrated example, the radiation monitoring system 400 comprises a server side radiation exposure monitoring application 410 arranged to implement at least a part of the inventive concept described herein. For example, the radiation exposure monitoring application 410 may comprise an integrated circuit having a signal processing module arranged to obtain radiation exposure information relating to procedures for which there exists a potential exposure of the patient to radiation; perform anatomical alignment of the obtained radiation exposure information; estimate a radiation dose per procedure; and calculate an aggregated radiation dose based at least partly on the estimated radiation doses.

Alternatively, the radiation exposure monitoring application 410 may comprise computer program code arranged to program one or more signal processor(s) (not shown) to perform a method for estimating a radiation exposure of a patient, such as the method illustrated in FIG. 1. In particular, the server side radiation exposure monitoring application may comprise computer program code for programming a computer system such as the computer system 600 illustrated in FIG. 6.

The server side radiation exposure monitoring application 410 is arranged to obtain information relating to procedures for which there exists a potential exposure of the patient to radiation, perform anatomical alignment of the obtained radiation exposure information, estimate a radiation dose per procedure, and calculate an aggregated radiation dose, based at least partly on the estimated radiation doses.

For example, the server side radiation exposure monitoring application 410 may be operably coupled to one or more client side user interface applications. It is contemplated that such client side user interface applications may be located locally with respect to the server side radiation exposure monitoring application 410, such as the local client side user interface application 420. For example, such a local client side user interface application 420 may be located on the same signal processing apparatus (for example the same personal computer or the like) as the server side radiation exposure monitoring application 410, and in some example embodiments being executed on the same signal processor (s). Alternatively, the local client side user interface application 420 may be located on a separate signal processing apparatus to the server side radiation exposure monitoring application 410, and coupled to the server side radiation exposure monitoring application 410 via a local network, such as a local area network (LAN), wireless local area network (WLAN), etc.

Additionally and/or alternatively, the server side radiation exposure monitoring application 410 may be operably coupled to one or more remote client side user interface applications, such as the remote client side user interface application 430 illustrated in FIG. 1. The remote client side user interface application 430 may be operably coupled to the server side radiation exposure monitoring application 410 by any suitable means. For example, the remote client side user interface application 430 may be operably coupled to the server side radiation exposure monitoring application 410 via a public network, such as the Internet (as illustrated in FIG. 4 at 440) or a public switched telephone network (PSTN), etc. Alternatively, the remote client side user interface application 430 may be operably coupled to the server side radiation exposure monitoring application 410 via a private connection or network, such as a wide area network (WAN) or the like.

It is contemplated that the server side radiation exposure monitoring application 410 may reside within (or comprise) an internet or Cloud service, for example in a similar manner to GoogleHealth™, Microsoft Healthvault™ or the like, and be accessible by way of web-based remote client side user interface applications, for example designed to run within a web-browser running on a computer or the like. As is known, such online services allow users to upload and keep patient's medical records, including imaging modality information and the like, in one place.

The server side radiation exposure monitoring application 410 may be arranged to receive information identifying a patient for which radiation exposure is to be estimated, for example from a client side user interface application 420, 430. Such information may comprise, by way of example only, patient name, demographic details, address, a patient identification number, etc.

The server side radiation exposure monitoring application 410 may then be arranged to obtain information relating to procedures for which there exists a potential exposure of the identified patient to radiation. As previously mentioned, such radiation exposure information may comprise information relating to one or more procedures previously performed on the patient for which there exists a potential for the patient to have been exposed to radiation. Additionally and/or alternatively, such radiation exposure information may comprise information relating to one or more prospective procedures yet to be performed on the patient for which there exists a potential for exposure of the patient to radiation. Furthermore, such information obtained may relate to any type of procedure for which there exists a potential exposure of the patient to radiation, such as any type of procedure involving ionising radiation.

The information relating to procedures for which there exists a potential exposure of the patient to radiation may be stored within one or more local data sources, such as local database 450 illustrated in FIG. 4 and accessible locally such as via a LAN or the like, and/or one or more remote data sources, such as remote databases 460, 470 illustrated in FIG. 4 and accessible by way of, say, the Internet 440. Accordingly, it is contemplated that the step of obtaining information relating to procedures for which there exists a potential exposure of the patient to radiation may comprise retrieving such information from one or more remote data sources and/or one or more local data sources. In accordance with some example embodiments, the server side radiation exposure monitoring application 410 may be arranged to search one or more databases that is/are accessible by the server side radiation exposure monitoring application 410 for information relating to procedures for which there exists a potential exposure of the patient to radiation. This can be achieved by searching for appropriate information using, for example, the patient name, demographic details, address, patient ID and similar search terms. The searching may be robust to typographic errors and variations in capitalisation and spelling, and also configurable such that a user, hospital and/or hospital group may tune (via a client side user interface application) the search appropriately. The server side radiation exposure monitoring application 410 may be further arranged to produce a list of potential patients with exact or similar matches, and also a secondary list of possible other matches. A user may thereby be able to select (via a client side user interface application) from the listed patients those for which information is to be obtained. The types of procedure for which information is obtained can comprise any that involves radiation exposure, and for example may comprise CT scans, X-Ray scans, PET scans, SPECT scans, PET/CT scans, SPECT/CT scans and other nuclear medicine scans such as planar bone scans, barium enema images and so forth. The server side radiation exposure monitoring application 410 may be configurable so that information relating to new types of procedure may be obtained.

Having obtained information relating to procedures for which there exists a potential exposure of the patient to radiation, the server side radiation exposure monitoring application 410 may then be arranged to perform anatomical alignment of the obtained information, for example as described in relation to step 140 of FIG. 1 above, and to estimating volumetric radiation doses per procedure for which radiation exposure information has been obtained, for example as described in relation to step 150 of FIG. 1 above. The server side radiation exposure monitoring application 410 may then calculate an aggregated volumetric radiation dose.

For example, the calculation of an aggregated volumetric radiation dose combines the estimated volumetric radiation doses per procedure and the anatomical alignment of the obtained radiation exposure information to produce an overall estimate of the aggregated radiation exposure from all of the procedures for which radiation exposure information has been obtained. The estimate may comprise a single aggregated radiation dose value representative of an overall exposure of the patient's body to radiation. Alternatively, it is contemplated that one or more estimates for anatomically localised aggregate radiation doses may be calculated, whereby such estimates may comprise one or more aggregated radiation dose value(s) that is/are representative of a more anatomically localised exposure to radiation for one or more parts of the patient's body. In accordance with some example embodiments, this step may comprise calculating anatomically localised aggregated radiation doses categorised into types of radiation. Furthermore, the time elapsed between exposures to radiation may be taken into consideration when calculating aggregated radiation doses in order to separately assess both short term and long term risks.

Figure 5:
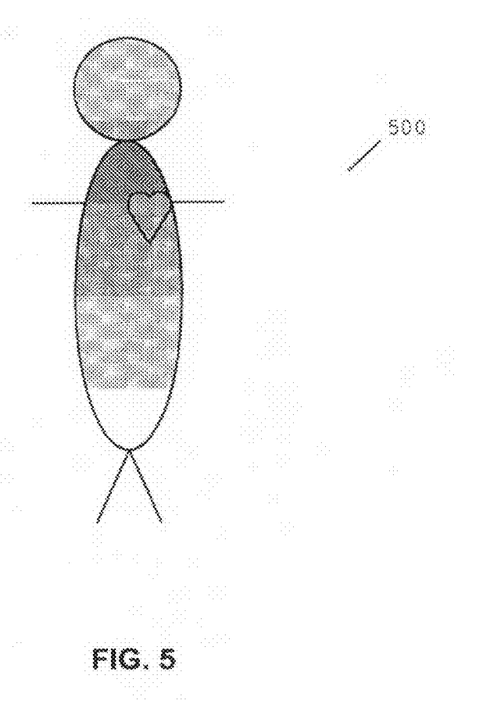
FIG. 5 illustrates an example of a reference image illustrating an aggregated radiation exposure.

The estimate of the aggregated radiation exposure may then be made available to a user, for example via a client side user interface application. For example, it is envisaged that the estimate of the aggregated radiation exposure may be accumulated on a 2D or 3D reference image allowing the dose to be examined and visualised in one representative image, for example as illustrated generally at 500 in FIG. 5. Technically, the accumulation maybe a simple summation of overall radiation or may be categorised according to the type of radiation, e.g. alpha, beta or gamma radiation. Furthermore, in some examples, it may be important to account for the time elapsed between exposures to help separate both short term and long term risk.

In accordance with some example embodiments, the server side radiation exposure monitoring application 410 may be arranged to run as a background process, whereby aggregated radiation exposure estimates for patients may be continuously calculated and updated as new information for those patients is added to existing database records. In this manner, server side radiation exposure monitoring application 410 may be able to provide an estimate of the aggregated radiation exposure for a patient substantially immediately, thereby minimising a delay to a user of the information. Alternatively, and in accordance with some alternative example embodiments, the server side radiation exposure monitoring application 410 may be arranged to calculate an estimate of the aggregated radiation exposure for a patient upon request by a user.

It is contemplated that a client side user interface application may be arranged to enable a user to provide information relating to or more prospective procedures yet to be performed on the patient for which there exists a potential for exposure of the patient to radiation, such that an estimate of aggregated radiation exposure may be calculated for the case that such prospective procedures were performed on the patient. In this manner, a user is able to assess the effect such procedures might have on the patient in terms of exposure to radiation. Furthermore, the client side user interface application may be arranged to compare estimates of the aggregated radiation exposure for a patient against guidelines and thereby show appropriate warnings. Such checks may be specific to parts of the body. For example, exposure to the reproductive organs might be of particular relevance for a person of a certain age intending to start a family. The client side user interface application may be arranged to also display an assessment of risk, either long term or short term, associated with the estimate of past radiation exposure or possible future exposure.

In accordance with some example embodiments, having calculated an estimate of the aggregated radiation exposure for a patient, the server side radiation exposure monitoring application 410 may be arranged to update such a calculated estimate upon receiving additional information relating to subsequently performed procedures becoming available. Such updating may be performed incrementally each time new information becomes available. Alternatively, such updating may be performed periodically, whereby a search for new information may be performed, and upon locating new information, the updating may be performed. Alternatively still, such updating may be performed upon request by a user. For example, upon obtaining information relating to subsequently performed procedures, the server side radiation exposure monitoring application 410 may be arranged to perform the steps of anatomical aligning the newly obtained information, and estimating volumetric radiation doses per procedure for the newly obtained information. The server side radiation exposure monitoring application 410 may then re-calculate the estimate of the aggregated radiation exposure for the patient based on the anatomical alignment and volumetric radiation dose estimates for all obtained radiation exposure information (both newly obtained and pre-existing).

Furthermore, it is contemplated that, having calculated one or more aggregated radiation exposure values for a patient based on radiation exposure information relating to one or more earlier procedures, the server side radiation exposure monitoring application 410 may be capable of calculating one or more further aggregated radiation exposure values for that patient corresponding to the one or more earlier procedures and one or more subsequent procedures based on the one or more aggregated radiation exposure values previously calculated for the earlier procedures and on radiation exposure information relating to the one or more subsequent procedures. For example, the server side radiation exposure monitoring application 410 may calculate one or more aggregated radiation exposure values for the subsequent procedures based on radiation exposure information therefor, and then add or otherwise combine the aggregated radiation exposure values for the subsequent procedures with the previously calculated aggregate radiation exposure values for the earlier procedures. In this manner, the server side radiation exposure monitoring application 410 does not require the radiation exposure information relating to the one or more earlier procedures in order to calculate updated aggregated radiation exposure values, but rather only previously calculated aggregated radiation exposure values for the earlier procedures. As a result, should such radiation exposure information relating to the one or more earlier procedures not be available, for example due to data loss or data retention policies, the server side radiation exposure monitoring application 410 is still capable of generating comprehensive aggregated radiation exposure values taking into account such earlier procedures through the previously calculated aggregated radiation exposure values.

It is contemplated that as new information relating to procedures becomes available, the server side radiation exposure monitoring application 410 may be arranged to examine images associated with newly obtained information and to re-assess the choice of reference image with which the obtained information is aligned. For example, if a whole body CT scan becomes available where previously only images relating to particular body parts were available, the server side radiation exposure monitoring application 410 may re-select the newly available whole body CT scan as the reference image with which to align the obtained information. The server side radiation exposure monitoring application 410 may further be arranged, upon selection of a new reference image, to re-calculate the estimate of the aggregated radiation exposure for the patient based on the newly aligned information.

Thus, for example embodiments of the present invention there are provided a method, integrated circuit and system for producing an aggregated estimate of radiation exposure for a patient that can be localised to parts of the body. In addition, the estimate uses information about the imaging study actually performed to estimate the exposure. Furthermore, information relating to different types of procedure involving radiation may be utilised, and the estimate may account for factors such as the energy and type of radiation used in the procedures, if that information is available, thereby leading to an improved estimate of not only radiation exposure but also of potential risks to the patient from such radiation exposure. Moreover, where, say, a scan is repeated several times during an imaging session due to the image quality being deemed to be insufficient in the initial scans, such multiple exposures may be taken into consideration, where such information is made available.

Figure 6:
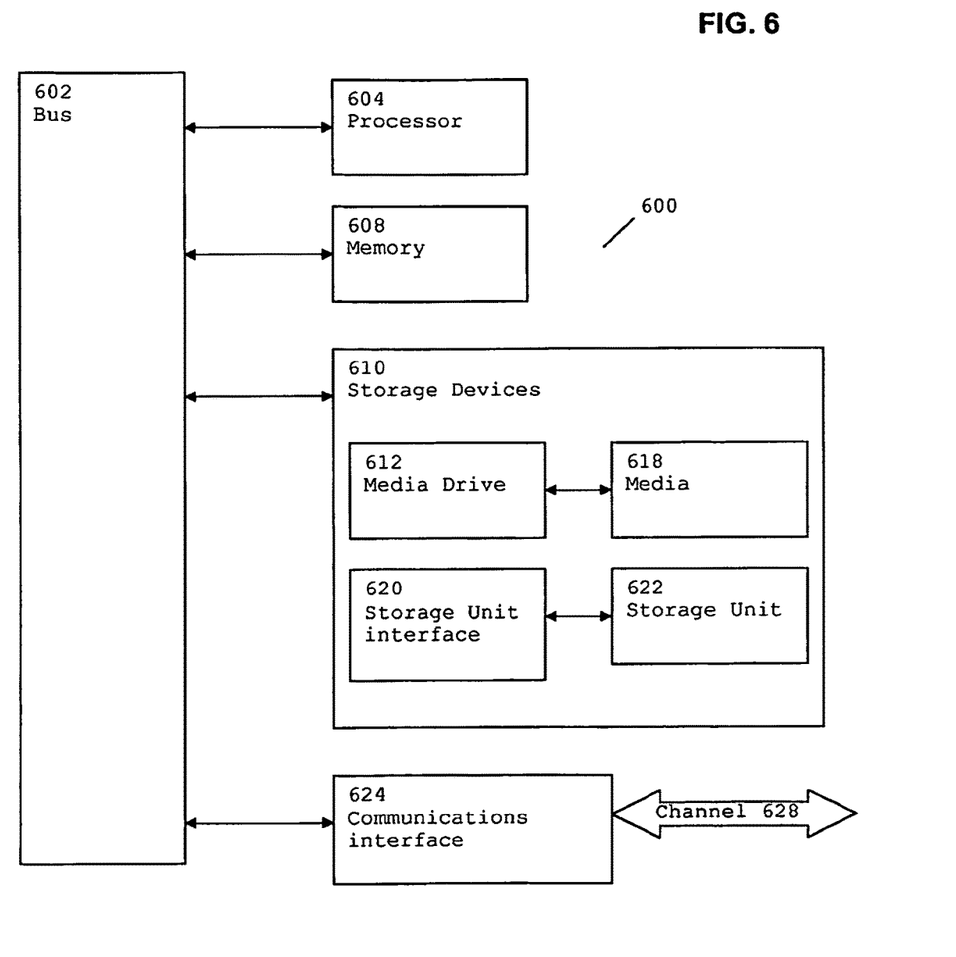
FIG. 6 illustrates a typical computing system that may be employed to implement signal processing functionality in embodiments of the invention.

Referring now to FIG. 6, there is illustrated a typical computing system 600 that may be employed to implement signal processing functionality in embodiments of the invention. Those skilled in the relevant art will also recognize how to implement the invention using other computer systems or architectures. Computing system 600 may represent, for example, a desktop, laptop or notebook computer, hand-held computing device (PDA, cell phone, palmtop, etc.), mainframe, server, client, or any other type of special or general purpose computing device as may be desirable or appropriate for a given application or environment. Computing system 600 can include one or more processors, such as a processor 604. Processor 604 can be implemented using a general or special-purpose processing engine such as, for example, a microprocessor, microcontroller or other control module. In this example, processor 604 is connected to a bus 602 or other communications medium.

Computing system 600 can also include a main memory 608, such as random access memory (RAM) or other dynamic memory, for storing information and instructions to be executed by processor 604. Main memory 608 also may be used for storing temporary variables or other intermediate information during execution of instructions to be executed by processor 604. Computing system 600 may likewise include a read only memory (ROM) or other static storage device coupled to bus 602 for storing static information and instructions for processor 604.

The computing system 600 may also include information storage system 610, which may include, for example, a media drive 612 and a removable storage interface 620. The media drive 612 may include a drive or other mechanism to support fixed or removable storage media, such as a hard disk drive, a floppy disk drive, a magnetic tape drive, an optical disk drive, a compact disc (CD) or digital video drive (DVD) read or write drive (R or RW), or other removable or fixed media drive. Storage media 618 may include, for example, a hard disk, floppy disk, magnetic tape, optical disk, CD or DVD, or other fixed or removable medium that is read by and written to by media drive 612. As these examples illustrate, the storage media 618 may include a computer-readable storage medium having particular computer software or data stored therein.

In alternative embodiments, information storage system 610 may include other similar components for allowing computer programs or other instructions or data to be loaded into computing system 600. Such components may include, for example, a removable storage unit 622 and an interface 620, such as a program cartridge and cartridge interface, a removable memory (for example, a flash memory or other removable memory module) and memory slot, and other removable storage units 622 and interfaces 620 that allow software and data to be transferred from the removable storage unit 618 to computing system 600.

Computing system 600 can also include a communications interface 624. Communications interface 624 can be used to allow software and data to be transferred between computing system 600 and external devices. Examples of communications interface 624 can include a modem, a network interface (such as an Ethernet or other NIC card), a communications port (such as for example, a universal serial bus (USB) port), a PCMCIA slot and card, etc. Software and data transferred via communications interface 624 are in the form of signals which can be electronic, electromagnetic, and optical or other signals capable of being received by communications interface 624. These signals are provided to communications interface 624 via a channel 628. This channel 628 may carry signals and may be implemented using a wireless medium, wire or cable, fiber optics, or other communications medium. Some examples of a channel include a phone line, a cellular phone link, an RF link, a network interface, a local or wide area network, and other communications channels.

In this document, the terms 'computer program product' 'computer-readable medium' and the like may be used generally to refer to media such as, for example, memory 608, storage device 618, or storage unit 622. These and other forms of computer-readable media may store one or more instructions for use by processor 604, to cause the processor to perform specified operations. Such instructions, generally referred to as 'computer program code' (which may be grouped in the form of computer programs or other groupings), when executed, enable the computing system 600 to perform functions of embodiments of the present invention. Note that the code may directly cause the processor to perform specified operations, be compiled to do so, and/or be combined with other software, hardware, and/or firmware elements (e.g., libraries for performing standard functions) to do so.

In an embodiment where the elements are implemented using software, the software may be stored in a computer-readable medium and loaded into computing system 600 using, for example, removable storage drive 622, drive 612 or communications interface 624. The control module (in this example, software instructions or computer program code), when executed by the processor 604, causes the processor 604 to perform the functions of the invention as described herein.

It will be appreciated that, for clarity purposes, the above description has described embodiments of the invention with reference to specific functional units. However, it will be apparent that any suitable distribution of functionality between different functional units, for example with respect to the server side radiation exposure monitoring application 410, may be used without detracting from the inventive concept. For example, functionality illustrated to be performed by a single instance of the server side radiation exposure monitoring application 410 may be performed by a plurality of server side radiation exposure monitoring functional units executing on a plurality of computer devices. Hence, references to specific functional units are only to be seen as references to suitable means for providing the described functionality, rather than indicative of a strict logical or physical structure or organization.

Aspects of the invention may be implemented in any suitable form including hardware, software, firmware or any combination of these. The invention may optionally be implemented, at least partly, as computer software running on one or more data processors and/or digital signal processors or configurable module components such as FPGA devices. Thus, the elements and components of an embodiment of the invention may be physically, functionally and logically implemented in any suitable way. Indeed, the functionality may be implemented in a single unit, in a plurality of units or as part of other functional units.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term 'comprising' does not exclude the presence of other elements or steps.

Furthermore, although individually listed, a plurality of means, elements or method steps may be implemented by, for example, a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category, but rather indicates that the feature is equally applicable to other claim categories, as appropriate.

Furthermore, the order of features in the claims does not imply any specific order in which the features must be performed and in particular the order of individual steps in a method claim does not imply that the steps must be performed in this order. Rather, the steps may be performed in any suitable order. In addition, singular references do not exclude a plurality. Thus, references to 'a', 'an', 'first', 'second', etc. do not preclude a plurality.

Thus, an improved radiation exposure monitoring system and method of operation therefor have been described, wherein the aforementioned disadvantages with prior art arrangements have been substantially alleviated.

What is claimed is:

1. A method for estimating radiation exposure of a patient arising from at least one medical image study of the patient and/or at least one radiation therapy procedure on the patient, the method comprising:

obtaining radiation exposure information relating to a plurality of procedures, the procedures comprising at least one diagnostic imaging procedure for which there exists a potential exposure of the patient to radiation and/or at least one radiation therapy procedure, wherein the obtained radiation exposure information comprises:
  anatomical images associated with the plurality of procedures for which radiation exposure information is obtained; and
  information from which radiation doses may be estimated for the plurality of procedures;
performing anatomical alignment of the obtained radiation exposure information to at least one three dimensional (3-D) reference image comprising three dimensional (3-D) voxels;
wherein performing the anatomical alignment comprises aligning, by an image registration algorithm, the anatomical images associated with the plurality of procedures to the at least one 3-D reference image, the at least one 3-D reference image comprising at least one of the anatomical images associated with the plurality of procedures for which radiation exposure information is obtained;
estimating a radiation dose per procedure based on the information from which radiation doses may be estimated for the plurality of procedures; and
calculating anatomically localised aggregated radiation doses for at least a region of the 3-D reference image, based at least partly on the anatomical alignment of the obtained radiation exposure information and the estimated radiation doses for the at least a region of the 3-D reference image, and corresponding regions of the anatomically aligned anatomical images.

2. The method of claim 1, wherein the method comprises obtaining radiation exposure information relating to at least one from a group comprising:
  at least one diagnostic imaging procedure previously performed on the patient for which there exists a potential for the patient to have been exposed to radiation; and
  at least one prospective diagnostic imaging procedure yet to be performed on the patient for which there exists a potential for exposure of the patient to radiation.

3. The method of claim 1, wherein the method comprises obtaining radiation exposure information relating to the at least one diagnostic imaging procedure of at least one from a group comprising:
  at least one X-Ray radiography scan;
  at least one Computed Tomography (CT) scan;
  at least one Single Photon Emission Computed Tomography (SPECT) scan;
  at least one Positron Emission Tomography (PET) scan;
  at least one nuclear medicine scan;
  at least one planar bone scan; and
  at least one barium enema scan.

4. The method of claim 1, wherein obtaining radiation exposure information relating to the at least one diagnostic imaging procedure for which there exists a potential exposure of the patient to radiation comprises retrieving such information from at least one from a group comprising: at least one remote data source, at least one local data source.

5. The method of claim 1, wherein the at least one 3-D reference image is selected from the anatomical images associated with the at least one diagnostic imaging procedure for which radiation exposure information is obtained based at least partly on at least one from a group consisting of:
  a type of procedure with which the at least one anatomical image is associated;
  a comprehensiveness of anatomical coverage of the at least one anatomical image;
  a resolution of the at least one anatomical image;
  information density of at least one anatomical image; and
  information content of at least one anatomical image.

6. The method of claim 1, wherein performing anatomical alignment of the obtained radiation exposure information comprises performing group-wise alignment of the anatomical images associated with obtained radiation exposure information sequentially to one another.

7. The method of claim 1, wherein performing anatomical alignment of the obtained radiation exposure information comprises aligning the radiation exposure information to anatomical regions within a predefined set of anatomical regions.

8. The method of claim 1, wherein estimating a radiation dose per diagnostic imaging procedure is based at least partly on at least one from a group comprising:
  a type of procedure for which a radiation dose is being estimated;
  at least one procedural specific attribute;
  at least one body part specific attribute;
  a volume of tissue exposed to radiation; and
  at least one patient specific attribute.

9. The method of claim 1, wherein the method comprises calculating anatomically localised aggregated radiation doses categorised into types of radiation.

10. The method of claim 1, further comprising comparing at least one calculated aggregated radiation dose to at least one threshold value, and if the at least one calculated aggregated radiation dose exceeds the at least one threshold value, generating a warning message.

11. The method of claim 1, further comprising:
  performing pre-matching to initialise the anatomical alignment.

12. A radiation exposure monitoring system comprising a signal processing module arranged to:
  obtain radiation exposure information relating to a plurality of procedures, the plurality of procedures comprising at least one diagnostic imaging procedure for which there exists a potential exposure of the patient to radiation and/or at least one radiation therapy procedure, wherein the obtained radiation exposure information comprises:
    anatomical images associated with the plurality of procedures for which radiation exposure information is obtained; and
    information from which radiation doses may be estimated for the plurality of procedures;
  perform anatomical alignment of the obtained radiation exposure information to at least one three dimensional (3-D) reference image comprising three dimensional (3-D) voxels;
  wherein performing the anatomical alignment comprises aligning, by an image registration algorithm, the anatomical images associated with the plurality of procedures to the at least one 3-D reference image, the at least one 3-D reference image comprising at least one of the anatomical images associated with the plurality of procedures for which radiation exposure information is obtained;
  estimate a radiation dose per procedure based on the information from which radiation doses may be estimated for the plurality of procedures; and
  calculate anatomically localised aggregated radiation doses for at least a region of the 3-D reference image based at least partly on the anatomical alignment of the obtained radiation exposure information and the estimated radiation doses for the at least a region of the 3-D reference image, and corresponding regions of the anatomically aligned anatomical images.

13. An integrated circuit comprising a signal processing module arranged to:
    obtain radiation exposure information relating to a plurality of procedures, the plurality of procedures comprising at least one diagnostic imaging procedure for which there exists a potential exposure of the patient to radiation and/or at least one radiation therapy procedure, wherein the obtained radiation exposure information comprises:
        anatomical images associated with the plurality of procedures for which radiation exposure information is obtained; and
        information from which radiation doses may be estimated for the plurality of procedures;
    perform anatomical alignment of the obtained radiation exposure information to at least one three dimensional (3-D) reference image comprising three dimensional (3-D) voxels;
    wherein performing the anatomical alignment comprises aligning, by an image registration algorithm, the anatomical images associated with the plurality of procedures to the at least one 3-D reference image, the at least one 3-D reference image comprising at least one of the anatomical images associated with the plurality of procedures for which radiation exposure information is obtained;
    estimate a radiation dose per procedure, based on the information from which radiation doses may be estimated for the plurality of procedures; and
    calculate anatomically localised aggregated radiation doses for at least a region of the 3-D reference image based at least partly on the anatomical alignment of the obtained radiation exposure information and the estimated radiation doses for the at least a region of the 3-D reference image, and corresponding regions of the anatomically aligned anatomical images.

14. A tangible computer program product having executable program code stored therein for programming signal processing logic to perform a method for estimating radiation exposure of a patient, the program code operable for, when executed at a computer system:
    obtaining radiation exposure information relating to a plurality procedures, the plurality of procedures comprising at least one diagnostic imaging procedure for which there exists a potential exposure of the patent to radiation and/or at least one radiation therapy procedure, wherein the obtained radiation exposure information comprises:
        anatomical images associated with the plurality of procedures for which radiation exposure information is obtained; and
        information from which radiation doses may be estimated for the plurality of procedures;
    performing anatomical alignment of the obtained radiation exposure information to at least one three dimensional (3-D) reference image comprising three dimensional (3-D) voxels;
    wherein performing the anatomical alignment comprises aligning, by an image registration algorithm, the anatomical images associated with the plurality of procedures to the at least one 3-D reference image, the at least one 3-D reference image comprising at least one of the anatomical images associated with the plurality of procedures for which radiation exposure information is obtained;
    estimating a radiation dose per procedure based on the information from which radiation doses may be estimated for the plurality of procedures; and
    calculating anatomically localised aggregated radiation doses for at least a region of the 3-D reference image based at least partly on the anatomical alignment of the obtained radiation exposure information and the estimated radiation doses for the at least a region of the 3-D reference image, and corresponding regions of the anatomically aligned anatomical images.

15. The tangible computer program product of claim 14, wherein the tangible computer program product comprises at least one of: a hard disk, a CD-ROM, an optical storage device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory.

* * * * *